US005567440A

United States Patent [19]

Hubbell et al.

[11] Patent Number: 5,567,440

[45] Date of Patent: Oct. 22, 1996

[54] METHODS FOR MODIFYING CELL CONTACT WITH A SURFACE

[75] Inventors: Jeffrey A. Hubbell; Donald Elbert; Jennifer L. Hill-West; Paul D. Drumheller, all of Austin; Sanghamitra Chowdhury, Round Rock, all of Tex.; Amarpreet Sawhney, Newtown, Mass.

[73] Assignee: Board of Regents, The University of Texas System, Austin, Tex.

[21] Appl. No.: 471,390

[22] Filed: Jun. 6, 1995

Related U.S. Application Data

[60] Division of Ser. No. 132,507, Oct. 5, 1993, Pat. No. 5,462,990, which is a continuation-in-part of Ser. No. 740,703, Aug. 5, 1991, Pat. No. 5,380,536, which is a division of Ser. No. 598,880, Oct. 15, 1990, abandoned.

[51] Int. Cl.⁶ .................................................. A61K 9/14
[52] U.S. Cl. ........................ 424/484; 424/485; 424/486; 424/488
[58] Field of Search ...................... 424/484, 485, 424/486, 488

[56] References Cited

U.S. PATENT DOCUMENTS

| | | | |
|---|---|---|---|
| 4,076,800 | 2/1978 | Marsh et al. | 424/70 |
| 4,352,883 | 10/1982 | Lim | 435/178 |
| 4,409,331 | 10/1983 | Lim | 435/178 |
| 4,434,150 | 2/1984 | Azad et al. | 424/1.1 |
| 4,663,268 | 5/1987 | Tsang et al. | 435/178 |
| 4,808,355 | 2/1989 | Goosen et al. | 424/424 |
| 4,923,645 | 5/1990 | Tsang et al. | 424/497 |

Primary Examiner—Nathan M. Nutter
Attorney, Agent, or Firm—Arnall Golden & Gregory

[57] ABSTRACT

Described herein is a multi-functional polymeric material for use in inhibiting adhesion and immune recognition between cells and cells, cells and tissues, and tissues and tissues. One component of the polymeric material adsorbs well to cells or tissue, and the other component of the polymeric material does not adsorb well to tissues. A water-soluble polymer that does not bear charge (polynonion) is used as the non-binding component, and a water soluble polymer that is positively charged at physiological pH (polycation) is used as the tissue binding component. When the bi-functional polymeric material contacts a tissue, the tissue-binding component binds and thus immobilizes the attached non-binding component, which will then extend generally away from the tissue surface and sterically block the attachment of other tissues. The method and compositions are useful in inhibiting formation of post-surgical adhesions, protecting damaged blood vessels from thrombosis and restenosis, and decreasing the extent of metastasis of attachment-dependent tumor cells.

25 Claims, 2 Drawing Sheets

FIG. 1

Agent      +      Tissue

→

Treated Tissue vs.

Cells Interacting with Tissue      Cells Interacting with Treated Tissue

METHODS FOR MODIFYING CELL CONTACT WITH A SURFACE

This is a divisional of prior application Ser. No. 08/132,507 filed on Oct. 5, 1993, by Jeffrey A. Hubbell, Donald Elbert, Jennifer L. Hill-West, Paul D. Drumheller, Sanghamitra Chowdhury, and Amarpreet Sawhney entitled "Multifunctional Organic Polymers," and now U.S. Pat. No. 5,462,990 which is a continuation-in-part of U.S. Ser. No. 07/740,703 filed on Aug. 5, 1991, now U.S. Pat. No. 5,380,536, which is a divisional of U.S. Ser. No. 07/598,880 filed on Oct. 15, 1990, now abandoned.

BACKGROUND OF THE INVENTION

This invention is generally in the area of organic polymer chemistry, specifically multifunctional polymers.

Cell adhesion plays an important role in human disease. These interactions proceed by the interaction of receptors upon the surface of a cell with proteins or glycosaminoglycans upon the surface of another cell or within the extracellular matrix. These receptors may be proteins or glycosaminoglycans.

Routes to the interruption of these interactions typically involve competitive inhibition of these receptor-ligand interactions, for example, with antibodies (e.g., anti-glycoprotein IIb/IIIa complex for anti-platelet therapy), soluble ligands which act as receptor antagonists (e.g., cyclic RGD peptides or von Willebrand factor fragments), soluble receptors, or other competitors.

It has also recently been demonstrated that it is possible to inhibit these interactions by mechanical means, for example, by photopolymerizing poly(ethylene glycol)-based hydrogels upon the cell, cell aggregate, matrix or tissue.

An example of the use of hydrogels to inhibit tissue adhesion is described by U.S. Pat. No. 5,126,141 to Henry. The process utilizes thermo-reversible gels of mixtures of polyoxyalkylene polymers and ionic polysaccharides applied to the tissues as liquids.

Unfortunately, the inhibitor based methods have a disadvantage common to many drug therapies, in that it is difficult to restrict the activity of the inhibitors to the region of interest. Hydrogel barriers are difficult to place and it is difficult to control chemical processes associated with them.

Isolated cells or tissues have also been protected from cell—cell contact, in this case from attack by immune cells, by placement within microcapsules formed of water soluble non-ionic polymers such as polyethylene oxide grafted to polycationic polymers such as poly-L-lysine. However, this is restricted to the use of isolated cells or tissues which are encapsulated within the polymer at the time of polymerization for subsequent implantation into the body.

It is therefore an object of the present invention to provide methods for making and using compositions, and the resulting compositions, for inhibiting tissue adhesion and cell—cell contact within the body.

It is a further object of the present invention to provide methods for making multifunctional polymeric materials which can be biodegradable and which can be used for drug delivery, either at a specific tissue-polymeric material interface or as a result of release of bioactive agents during degradation of polymeric material.

SUMMARY OF THE INVENTION

A bi-functional polymeric material for use in inhibiting cell—cell contact and tissue adhesion is disclosed wherein one domain of the material (i.e., one region with a particular function) is a polymer which adsorbs to cells or tissue (referred to collectively below as "tissue"), and the other domain of the polymeric material is a polymer which does not adsorb to tissue. Since most tissues bear a net negative charge, a positively charged polymer (polycation) is used as the tissue-binding domain. A water-soluble polymer that does not bear charge (polynonion) is used as the non-binding domain. When the two-domain polymeric material contacts a tissue, the tissue-binding domain(s) binds and immobilizes the attached non-binding domain(s), which then generally extends away from the tissue surface and sterically blocks the attachment of other tissues.

Additional domains, linking groups, and bioactive materials can be added to this basic two-domain structure to confer, for example, adhesion to particular types of cells or molecules or degradation by enzymatic or non-enzymatic means. These domains may be a third type of polymer, or when serving to direct attachment, a peptide such as RGD, or even a single amino acid, which is used to target a polyamino acid for cleavage by an enzyme.

The polymer is applied in a fluid phase to the tissues or cells to be protected, whereupon the tissue binding domains adsorb the polymeric material to the tissue. The fluid phase can be applied to isolated tissue or to tissue during surgery or by means of a catheter or other less invasive device.

The compositions are useful for blocking adhesion and immune recognition and thus may be useful in the treatment of many diseases, including the prevention of postoperative adhesions, protecting injured blood vessels from thrombosis and intimal thickening relating to restenosis, and decreasing the extent of metastasis of tumor cells in tissues.

DETAILED DESCRIPTION OF THE INVENTION

I. General Structures of the Polymers

There are three general structures of the polymeric materials described herein. Each structure is a block copolymer, i.e., a polymer composed of connecting multiple polymer chains of different composition. The three structures are (1) brush copolymers (as in a bottle brush, with a backbone of one composition and bristles of another) with a backbone of poly(B) and bristles composed of poly(A), (A)x-b-(B)y; (2) AB block copolymers, i.e., (A)x(B)y, or a poly(A) connected at one end to a poly (B); and (3) ABA block copolymers, i.e., (A)x(B)y(A)z, or a poly(A) connected at both ends to poly(A) chains, or in a less preferred embodiment, (B)x(A)y(B)z; where A is a monomer, the polymer of which does not bind strongly to a tissue; B is a monomer, the polymer of which does bind strongly to a tissue; x is an integer of greater than or equal to 5; y is an integer of greater than or equal to 3; and z is an integer greater than or equal to zero. As used herein, "polymeric materials" include polymers of oligomers. X is determined as that number providing the desired degree of repulsiveness or non-adhesiveness to tissue; y is determined as that number providing the desired degree of adhesiveness of the polymeric material to tissues, as discussed in more detail below. Poly(A) and poly(B) are generally linear polymers, although both may be linear or branched. Both A and B can be monomers, macromers or polymers.

A. Selection of "(B) n"

"(B)n" can be any biocompatible water-soluble polycationic polymer, for example, any polymer having protonated heterocycles attached as pendant groups. As used herein, "water soluble" means that the entire polymer, poly(B)y, must be soluble in aqueous solutions, such as buffered saline or buffered saline with small amounts of added organic solvents as cosolvents, at a temperature between 20° and 37° C. In some embodiments, poly(B) will not be sufficiently soluble in aqueous solutions per se but can be brought into solution by grafting with water-soluble poly(A) chains. Examples include polyamines having amine groups on either the polymer backbone or the polymer sidechains, such as poly-L-lysine and other positively charged polyamino acids of natural or synthetic amino acids or mixtures of amino acids, including poly(D-lysine), poly(ornithine), poly(arginine), and poly(histidine), and nonpeptide polyamines such as poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan.

B. Selection of "(A)n"

Any biocompatible, preferably polynonionic at a pH of between 6.5 and 8.5, polymer that does not bind to tissue can be used as (A)x. These include poly(oxyalkylene oxides) such as poly(ethylene oxide), poly(ethyloxazoline), poly(N-vinyl pyrrolidone), poly(vinyl alcohol), and neutral poly(amino acids) such as poly(serine), poly(threonine), and poly(glutamine) and copolymers of the monomers thereof, polysaccharides such as dextran, water soluble cellulose derivatives such as hydroxy ethyl cellulose, poly(hydroxyethyl acrylate), poly(hydroxy ethylmethacrylate) and polyacrylamide.

In some cases, polymers that bear a net negative charge (polyanion) will also function well as the non-binding domain, but only in cases where the interaction between the polycation and the polyanion is such that the two-domain polymer does not precipitate due to the interactions between the opposite charges. When polyanionic polymers are mixed with polycationic polymers, the mixture often precipitates due to the interaction of the opposite charges on the two polymers. The extent to which this occurs depends upon the nature of the charges of the particular polymers in question, as well as their solvent environment. Such precipitation may also occur with the block copolymers, if polyanions are used as the (A)x domains. There may, however, be polyanion (A)x and polycation (B)y combinations that will not precipitate, which may be determined experimentally by those of ordinary skill in the art. In particular, (A)x comprising weak acids such as polyalcohols may be expected to behave in this way. Polyalcohols are such weak acids that they may be considered for the purposes described herein as being essentially polynonionic. Negatively charged polymers from polyacids may also be determined to form stable, soluble copolymers with suitable polycations in useful aqueous formulations.

It should also be understood that the (A)x and the (B)y blocks could themselves be copolymeric, so long as they retain their dominant polynonionic (for (A)x) or polycationic (for (B)y) character. For example, an (A)x could consist of a copolymer of ethylene oxide and another water-soluble, nonionic comonomer, and a (B)y could consist of a copolymer of lysine and another amino acid with a cationic (e.g., arginine) or nonionic (e.g., glycine) side chain.

An example of a preferred polymeric material as described herein is formed of poly(L-lysine) (abbreviated PLL), "(B)y", and poly(ethylene oxide), also known as poly(ethylene glycol) or poly(oxyethylene) (abbreviated PEG), "(A)x". The end groups on the PEG should not be considered as specified by the name PEG.

Block copolymers of PLL and PEG are useful two-domain polymeric materials, where the PEG domain, which does not bind well to tissues, is immobilized upon a tissue by the adsorption of the PLL, which does bind well to the tissue.

In general, the molecular weight of (B)y must be sufficient to yield the desired degree of binding, generally including at least five charges, and having a molecular weight of at least 300 g/mole. In general, the molecular weight of (A)x must be sufficient to provide the desired degree of repellency of tissue or macromolecules, taking into consideration potential steric hindrance of the polymer, generally requiring a molecular weight of at least 300 g/mole. The lengths of the (A)x and the (B)y in the domains which would result in good blockage of adhesive and immune interactions may be determined by routine experimentation. In general, the larger the ratio of (A)x mass to (B)y mass, the weaker the binding of the polymer and the stronger the repulsion of potentially attaching tissues would be. Thus, the function of the polymer is used to determine an optimum amount of (B)x required to yield good binding and the optimum amount of (A)y to yield good repulsion. It should be understood that "good" is a word that must be defined by the requirements of the particular circumstance at hand, e.g., how long binding is required and how complete a repulsion is required by the particular medical application. In addition to the mass ratio of (A)x to (B)y, the number of chains of (A)x and the number of chains of (B)y may be varied from many A:B to 1 A:B in (A)x-b-(B) y; to 2 A:B in (A)x(B)y(A)z; to 1 A:B in (A)x(B)y), as can the absolute lengths of the two chains (e.g., an (A)x-b-(B)y with a particular mass fraction of A:B with many short (B)y may function in a different manner than one with a few long (B)y chains).

II. Specialized Structures of the Polymers

Modifications of the bi-functional polymers are shown diagrammatically below. The first functionality is the characteristic of tissue adsorbancy, determined by (B)y. The second functionality is the characteristic of not adsorbing to tissue, or tissue repellency, determined by (A)x.

```
 A   A   A
 A   A   A
BBBBBBBBBBB      AAABBBBBBBBAAA      AAABBBB (Brush Block      (ABA Block          (AB Block
 Copolymer)        Copolymer)          Copolymer)
``` wherein:

A denotes a domain that does not adsorb well to tissues; and

B denotes a domain that adsorbs well to tissues, such as the polycation poly-L-lysine (PLL).

When present on the tissues, the two-domain polymers will adsorb to the tissues in a conformation that could be graphically represented as follows, where the solid line represents the tissue surface:

```
 A  A  A        A       A      A
 A  A  A        A       A      A
 A  A  A        A       A      A
BBBBBBBBBBB     BBBBBBBB       BBBB
___________     ________       ____

(Brush Block    (ABA Block     (AB Block
 Copolymer)      Copolymer)    Copolymer)
```

As shown above, the B component adsorbs well to the tissue, and the A component, which has no strong interaction with the tissue, dangles generally away from it. The net effect of the adsorption of the dual function polymeric material is to link to tissue the A component, which by itself does not bind well to tissues, thus blocking the adhesion of other cells, tissues, or macromolecules to the treated surface.

Although described herein with reference to (A)x consisting of a single polymer, the structures shown diagrammatically above can be synthesized using mixtures of polymers as (A)x. For example, the "bristles" on the brush polymers could be formed of different (A)x, $(A)x_1$, $(A)x_2$, $(A)x_3$, etc., as could the termini on the AGA block copolymers. These embodiments consisting of one or more types of polymers (A)x are referred to jointly herein as (A)x.

ABA block copolymers are expected to be more effective in repelling tissues than BAB block copolymers, i.e., with a central nonbinding block and peripheral binding blocks. However, there may be cases where BAB block copolymers demonstrate high binding to the tissues and high degrees of repulsion of approaching tissues. This is especially true with the use of strongly binding, short (B)y regions with a long central (A)x region.

A. Control of Duration of Binding

It may be desirable to control the duration of the repulsiveness of the polymeric material or the duration of the presence of the polymeric material. There are several ways in which this can be accomplished. These are generally divided into (1) selection of (B)y on the basis of the strength, or lack of strength, of binding over time to tissue; (2) modification of the polymeric material to incorporate a domain C resulting in degradation of the polymeric material and/or separation of the binding component (B)y from the repulsive component (A)x; and synthesis of polymeric material where either the binding component (B)y is converted into a non-binding component (D)y or the repulsive component (A)x is converted into a non-repulsive or binding component (F)y.

1. Selection of Type and Relative Ratios of Binding and Repulsive Components In the first case, it may be desirable to control the duration of the binding of the polymer to the treated tissue by controlling its rate of desorption. Such control may be desirable to control the duration of repulsiveness or to control its presence for regulatory or toxicological concerns. Control can be achieved in several ways. Various (B)y would be expected to bind to the tissue with different strength. For example, a poly(L-histidine) would be expected to bind to tissues less strongly than a poly(L-arginine) of the same chain length (i.e., same y in (B)y), because a lower fraction of the histidine residues are charged at physiologic pH than of the arginine residues. The stronger the binding of the (B)y, the longer the duration of binding would be. The strength of binding of various (A)x-b-(B)y, (A)x(B)y, and (A)x(B)y(A)z will depend upon the particular structure of the polymer and upon the ratio of mass of (A)x to (B)y. In either of these cases, the duration of binding is determined by the rate of desorption without any chemical changes in the polymer.

2. Incorporation of Degradable Regions or Cleavage Sites into the Polymers

A component which is subject to degradation can be selected to control the duration of the presence of or the repulsion of the polymer. This can be accomplished by selecting an (B)y that is degraded by nonenzymatic hydrolysis, such as a polyester, polyamide, polyurethane, or polyanhydride; or that is degraded by enzymatic hydrolysis, such as a polypeptide or polysaccharide. Oxidative mechanisms may also be utilized to achieve degradation. For example, ether, urethane, and tertiary carbon structures are known to be sensitive to oxidative degradation. The use of these structures in the copolymer may lead to degradation by reactions, e.g., nitric oxide, peroxynitrite, or hypochlorite. Homopolymeric backbones or regions (B)y are expected to have differential stability to nonenzymatic or enzymatic degradation in vivo, e.g., poly-L-lysine, poly-D-lysine, polyornithine, polyhistadine, and polyarginine should display differential stability. For example, poly(D-lysine) would be expected to be more resistant proteolytic degradation than poly(L-lysine).

The polymeric material can be targeted for cleavage by an enzyme by including a recognition amino acid or recognition sequence for an enzyme within the polymeric material. This targeting component is referred to herein as "C". In general, the enzyme will be a naturally occurring protease such as trypsin, thrombin, factor XII, factor XIII, other coagulation factors, collagenase, elastase, plasmin, or other endoprotease or ectoprotease which recognize specific amino acid sequences. Individual amino acids can be incorporated into the polymer to make the polymer sensitive to degradation by less specific proteases. Saccharide or oligosaccharide regions which are cleaved by a variety of enzymes present in tissues, such as amylases, could also be used.

Component C could also be selected to be sensitive to nonenzymatic hydrolysis, for example, a dimer of lactic acid, the ester of which is sensitive to hydrolysis. In this way, the non-binding (A)x is cleaved from the (B)y, separating the polymeric material into its two components, one of which no longer binds and the other which no longer repels tissue. Other nonenzymatically sensitive sites could also be selected, such as other esters, amides, anhydrides, and numerous others apparent to those skilled in the art of degradable polymers.

Considerable tailoring of this loss of repulsiveness may be obtained by controlling how the repulsive bristles fall off via the cleavage or degradation of component C. This degradation may be controlled by the action of water without any enzymatic activity, and thus would be solely a function of time, or by the action of an enzyme. Two types of enzyme sensitivities could be selected: a sequence that is sensitive to a constitutively expressed enzyme, e.g., coagulation factor Xa, so that degradation would still be mostly a function of time, or one could select a sequence that is sensitive to a regulated enzyme, such as plasmin or collagenase, both of which are expressed at the leading edge of many types of migrating cells during healing. This would allow a cell, during healing, to wipe away the repulsiveness that was protecting the surface prior to healing.

In terms of timing the duration of the presence of the material, degradation of the adsorbing region B would result in removal of the polymeric material from the surface of the tissue. This may be important from the perspectives of both optimal efficacy and regulatory approval, where the minimum residence of the polymeric material in the body is desired.

Different embodiments of these modifications can be designed, for example, the (A)x can be connected to the (B)y via a linker C, to form (A)xC-b-(B)y, (A)xC(B)y, or (A)xC(B)yC(A)z. These embodiments are shown schematically below.

the backbone of the polymer may be selected to undergo a nondegradative chemical transformation to alter its affinity for the tissue.

In one embodiment, one can obtain desorption by converting the (B)y region to a nonadsorbing region, (D)y, either by the action of water or through the use of a constitutive or regulated enzyme. For example, poly(L-glutamic acid) could be selected as a backbone. This polymer does not bind well to tissues since it is polyanionic. It can be converted to a tissue-binding polymer by esterification with a compound such as bromoethylamine hydrochloride, or by amidification with a compound such as ethylene diamine. The esters and amides are hydrolytically sensitive and will, with time, be converted back to poly(L-glutamic acid) and ethanolamine or ethylene diamine, with the poly(L glutamic acid) region readily desorbing. For example, the side chain carboxyls are esterified with ethanolamine (amine protected), so that subsequent hydrolysis of the ester in vivo releases the (binding, B) amine to produce a (non-binding, D) carboxyl. Alternatively, the side chain carboxyls may be amidated with ethylenedianime (one amine protected), and subsequent hydrolysis of the amide in vivo releases the (binding, B) amine to produce a (nonbinding, D) carboxyl.

This embodiment is shown diagrammatically below:

At longer times:

```
  A  A  A                                        A  A  A
  A  A  A —\                   A  A  A    or    A  A  A
  A  A  A —/                   A  A  A          A  A  A
  C  C  C                      A  A  A          C  C  C
BBBBBBBBBB
                             BBBBBBBBBB        BBBBBBBBBB
```

(Brush Block Copolymer)          (C degrades and agent
with Degradation-labile           diffuses away; long B
Bristles)                         segments remain)

At longer times

```
  A  A                        A  A  A           A  A  A
  A  A  A —\                  A  A  A    or     A  A  A
  A  A  A —/                  A  A  A           A  A  A
BBCBBCBBCB                   BB BB BB B        BBC BBC BBC B
```

(Brush Block Copolymer)          (C degrades and agent
with Degradation-labile           diffuses away;
Backbone                          short B segments desorb)

wherein
C denotes a cleavage site, for example, for cleavage via enzymatic or nonenzymatic hydrolysis.

3. Selection of (A)x or (B)y which is Converted into Domains Having Different Binding Affinities The duration of binding may also be controlled by designing chemical sensitivities into the polymers. For example,

```
At short times       At longer times      At even longer
times
  A  A  A              A  A  A              A  A  A
  A  A  A    ─→        A  A  A    ─→        A  A  A
  A  A  A              A  A  A              A  A  A
BBBBBBBBBB            BDBDBBDBBDD          DDDDDDDDDD
```

(Brush Block              (B, which binds,         (Polymer
Copolymer with            converting to D,         desorbs)
Reactively-               which does not bind)
labile Backbone)

wherein

D denotes a nonbinding group which arises by reaction of B, a binding group. B converts into D after binding.

In another embodiment, one can design nonadhesive components (A)x that react in vivo to yield domains consisting of (E)x that are no longer repulsive. For example, a polyamine could be selected as the adhesive component. The amine groups could be protected by reaction with a carboxyl-containing group, such as a (hydroxyl protected) hydroxy acid (with subsequent deprotection). The resulting amide bond would render the original amine much less adhesive and more repulsive, yielding the A)x component. Over time, hydrolysis of the amide bond would result in loss of the hydroxy acid, forming the original amine, which would increase adhesiveness and decline in repulsiveness. Such chemical conversions in vivo could occur nonenzymatically, as described above, or enzymatically, either by a constitutively present or regulated enzyme, as described further above.

This is described diagrammatically below.

| At short times | At longer times | At even longer times |
|---|---|---|
| A A A | A A E | E E E |
| A A A | E A E | E E E |
| A A A | A E A | E E E |
| BBBBBBBBBBB | BBBBBBBBBBB | BBBBBBBBBBB |
| (Brush block copolymer with reactively labile bristles) | (A, which repels, converting to E, which does not repel) | (polymer loses its repellency) | wherein

E denotes an adhesive group, which arose by reaction of A, a repulsive group.

In summary, the overall adsorption of the polymer to a tissue, and then its repulsion of other tissues, is an optimization: with much (B)y, adsorption will be strong, but subsequent repulsion will be weak; and with much (A)x, repulsion will be strong, but adsorption will be weak.

There are at least two general ways to determine the duration of repulsiveness: (1) by timing the duration of the presence of the polymeric material on the tissue surface, e.g., by timing degradation of the backbone, reaction of (A)x or (B)y to result in desorption, or desorption without degradation by varying binding affinity of (B)y; and (2) by timing the duration of the repulsiveness of the polymeric material on the surface, e.g., by timing the degradation of the repulsive components (A)x or reaction of (A)x to result in loss of repulsion.

B. Attachment of Bioactive Species

Additional activities may be added to the polymeric material by attaching bioactive species ("F") to the ends of the (A)x, elsewhere on the (A)x, or onto the (B)y. Such bioactive species may be adhesion peptides, adhesion oligosaccharides, antibodies, enzymes, receptor ligands, or drugs. Bioactive species may be used to target adhesion of the polymeric material, to effect a biological activity at the polymeric material-tissue interface, or to effect an activity when released during degradation of the polymeric material.

For example, the adhesion peptide Tyr-Ile-Gly-Ser-Arg, from laminin, binds to receptors on endothelial cells, but not on blood platelets. Thus, the addition of the oligopeptide Tyr-Ile-Gly-Ser-Arg to the termini of the (A)x and adsorbing the polymeric material to a damaged vessel wall would be expected to block thrombosis on the vessel wall but not to block reendothelialization from the surrounding undamaged vessel wall. This embodiment makes it possible to cover the thrombogenicity of an injured vessel wall but, via an adhesion ligand F on the termini of the (A)x components, to permit the regrowth of endothelial cells upon the polymer. In this case, F is the pentapeptide Tyr-Ile-Gly-Ser-Arg (YIGSR), which supports endothelial, smooth muscle cell, and fibroblast adhesion, but not platelet adhesion; or the tetrapeptide Arg-Glu-Asp-Val (REDV), which has been shown to support endothelial cell adhesion but not that of smooth muscle cells, fibroblasts, or platelets, J. A. Hubbell, et al., "Endothelial cell-selective materials for tissue engineering in the vascular graft via a new receptor *BioTechnology* 9:568–572 (1991), the teachings of which are incorporated herein. This approach also permits the reendothelialization of the vessel wall while it is still not adhesive to platelets, thus enabling healing while avoiding platelet activation and thrombus formation.

In another embodiment, an enzyme F is coupled to the (A)x termini, thereby covering up the platelet reactivity of the damaged vessel (in angioplasty injury) or mesothelium (in pelvic adhesions) while at the same time immobilizing a beneficial biological activity. Examples of useful enzymes include tissue plasminogen activator (tPA), since plasminogen activation is desirable in both prevention of pelvic/abdominal adhesions and in the resorption of vascular thrombus. Numerous other bioactive species may be beneficial.

This embodiment is shown schematically as:

```
F F F
A A A
A A A
A A A
BBBBBBBBBBB
```
(Brush Block Copolymer with Bioactive agent-terminated bristles)

wherein

F=Bioactive agent.

III. Synthesis of Polymers

In general, methods for synthesis of the different polymeric materials will be apparent to those skilled in the art from the foregoing description.

A. Brush Block Copolymers

1. Method for Grafting A upon the ε Amines of B, with all the ε Amines Deprotected, Using Stoichiometric Control in Water PEG may be bonded to the ε-amines of lysine residues of poly(L-lysine) as follows. Poly(L-lysine) (PLL) is reacted with monomethoxy PEG, the terminal hydroxyl of which has been previously activated with carbonyldiimidizole (CDI). The PLL and the activated PEG are mixed in an aqueous solution buffered at pH 9 and allowed to react for 48 hours at room temperature. The number of PEG chains grafted per PLL chain may be controlled by the ratio of moles activated PEG added per mole PLL added. The reaction may not proceed to completion, i.e., the mole ratio of PEG to PLL in the reaction mixture may not be identical to that in the PEG-b-PLL product, but higher ratios of PEG to PLL will produce higher amounts of PEG in the PEG-b-PLL product.

2. Method for Grafting A onto the ε Amines of B, with all the ε Amines Deprotected, Using Stoichiometric Control in Anhydrous Solvent The cationic domains tend to be highly reactive, and efforts must be made to control the extent of addition of "A" to "B". Executing the reaction in the absence of water reduces deactivation of "A" and allows better stoichiometric control. For example, unprotected poly-L-lysine is dissolved in water, then added to dimethylformamide (DMF) to make a solution that is 5% aqueous. The poly-L-lysine is then reacted with CDI mono-activated PEG in stoichiometric amounts, followed by evaporation of solvent under vacuum yielding an (A)x-b-(B)y copolymer. Alternatively, unprotected poly-L-lysine is dissolved in water and is precipitated by addition of NaOH. The precipitated polymer is added to anhydrous DMF and then reacted with CDI mono-activated PEG in stoichiometric amounts, yielding an (A)x-b-(B)y copolymer. When the reaction is performed in the absence of water, side reactions involving the activated group are reduced (i.e., deactivation is reduced), and at long reaction times the ratio of mole PLL to PEG in the polymer product more closely resembles than in the reactant mixture.

3. Grafting A upon the ε Amines of B, with a Controlled Number of Those Amines Deprotected Solution polymerization of PLL may be carried out using monomers containing different epsilon protecting groups, which allows strict control over the degree of substitution of "A" onto "B". N-carboxy anhydrides of various amino acids may be synthesized and polymerized into copolymers, as in the following example. N,N'-dicarbobenzoxy-L-lysine (Z,Z-lysine) is reacted with phosphorus pentachloride to yield ε,N-carbobenzoxy-α,N-carboxy-L-lysine anhydride. α,N-carbobenzoxy-ε,N-tert-butyloxycarbonyl-L-lysine (Z,boc-lysine) is reacted with sodium methoxide to yield the sodium salt of Z,boc-lysine. The sodium salt of Z,boc-lysine is reacted with phosphorus pentachloride to yield ε,N-tert-butyloxycarbonyl-α,N-carboxy-L-lysine anhydride. Z,Z-lysine anhydride is added to Z,boc-lysine anhydride, and the two monomers are polymerized by the addition of sodium methoxide as an initiator. A copolymer results, poly(ε boc-lysine)-co-(ε Z-lysine). The boc groups are removed by addition of the polymer to trifluoroacetic acid for fifteen minutes. The salt form is converted to the free base by reaction with a reactant such as pyridine. The free amines on the polymer are then reacted with CDI PEG in DMF. The Z groups are deprotected by addition of the polymer to HBr in acetic acid for fifteen minutes, yielding an (A)x-b-(B)y copolymer, where the ratio of PEG to PLL in the final product is controlled by the inital ratio of boc protected lysines, which were ultimately grafted with PEG, to Z protected lysines, which were not grafted.

As an alternative to solution polymerization, greater control over the length of the "B" segment may be obtained through the use of solid phase orthogonal synthesis. For example, poly-L-lysine is synthesized using a peptide synthesizer. The monomer lysines used in the synthesis are of two types. One type of lysine is α-amine protected using the F-moc protecting group (9-fluorenylmethyloxycarbonyl group), and is ε-amine protected with the Z protecting group (benzyloxycarbonyl group). The second type of lysine is α-amine protected using the F-moc protecting group, and is ε-amine protected with the t-Boc protecting group (tert. butyloxycarbonyl group). A thirty residue peptide is constructed, with one t-boc protected lysine per nine Z protected lysines. The t-boc groups are selectively cleaved by immersion of the peptide in neat trifluoroacetic acid for fifteen minutes, and then desalted with pyridine. The free amines are reacted with CDI mono-activated PEG in DMF. The Z groups are then deprotected with HBr in acetic acid for 15 minutes, yielding an (A)x-b-(B)y copolymer.

4. Solid Phase Synthesis of PLL Copolymerized with Another Residue, the Side Groups of which are Used for Grafting of A Not only may the protecting groups be varied, but the type of residue may also be changed. For example, on a peptide synthesizer, a peptide is made utilizing both Z protected lysine and tert. butyl protected aspartic acid in a ratio of nine lysines per one aspartic acid. The tert. butyl group is deprotected by immersion of the polymer in neat trifluoroacetic acid. The free carboxyl groups are activated with O-(N-Succinimidyl)-N,N,N',N'-tetramethyluronium tetrafluoroborate (TSU) in DMF. The TSU activated peptide is reacted with mono-amine-PEG in DMF. The Z protecting groups on the lysines are removed by incubation of the peptide with HBr in acetic acid, yielding an (A)x-b-(B)y copolymer.

B. AB (and ABA) Block Copolymers

1. Grafting A to the Terminal Amine (and Carboxyl) Prior to Deprotection of the ε Amines It may be desirable to produce versions of the polymer which are not of a brush structure. This may be facilitated by not deprotecting the epsilon amines of PLL, so that the only reactive groups are the amine and carboxyl termini. For example, reaction of CDI mon-activated PEG with poly ε,N-carbobenzoxy-L-lysine in DMF yields an (A)x-(B)y copolymer. Activation of the carboxyl terminus of the (A)x-(B)y copolymer with TSU followed by reaction with mono-amino PEG in DMF yields an (A)x-(B)y-(A)z copolymer.

2. Solid Phase Synthesis of PLL Using Two Monomer Lysines with Different Amine Protection Chemistries, the N (and C) Terminal Residue(s) Being Differently Protected than the Other Lysine Residues The presence of a free amine on both ends of the "B" segment would require fewer reactions to attach "A" segments to the ends of the polymer. This may be done by beginning the synthesis with a residue containing an epsilon protecting group which may be removed without disturbing the other epsilon protecting groups. The "A" chain reacts with this free amine, as well as the free amine at the N terminus of the peptide. For example, poly ε,N-carbobenzoxy-L-lysine is synthesized by solid phase methods, and the ε-residue at the carboxyl terminus is boc protected, with all other ε-residues Z protected. The boc is removed in trifluoroacetic acid, and the free amines are reacted with CDI mono-activated PEG in DMF. The Z groups are removed with HBr in acetic acid, yielding an (A)x-(B)y-(A)z copolymer.

3. Solid Phase Synthesis of PLL Copolymerized With Another Residue, the N (and C) Terminal Residues Being the Different Composition, the Side Group(s) of which will be Used for Grafting of A Beginning the synthesis of a pure poly-L-arginine chain with a lysine will place a reactive amine at both ends of the poly-L-arginine chain. The poly-L-arginine would be the "B" binding segment, and "A" segments could be placed onto the amines. For example, poly-L-arginine is synthesized by solid phase methods, but the residue at the carboxyl terminus is a boc protected lysine. The boc group is removed in trifluoroacetic acid, and the peptide is reacted with CDI PEG in pH 9 buffered water, yielding an (A)x-(B)y-(A)z copolymer, with the (B)y segment representing poly-L-arginine.

The following examples are exemplary of methods of synthesis for the specialized modified embodiments of the polymeric materials.

4. Solution Phase Polymerization of N-carboxyl Anhydride Lysine with PEG as Initiator to Yield AB Copolymer In the solution phase polymerization of a polyamino acid, the sodium salt of the PEG may be used as an initiator. For example, the polymerization of the N-carboxy anhydride of lysine is initiated by the sodium salt of monomethoxy PEG, as described by Pratten, M. K., Lloyd, J. B., Horpel, G., Ringsdorf, H., "Micelle-forming block copolymers: Pinocytosis by macrophages and interaction with model membranes", *Makromol. Chem.* 186, 725–33 (1985).

5. Polymerization of Ethylene Oxide with PLL as Initiator

Ethylene oxide is polymerized to PEG by the addition of an initiator, with incorporation of the initiator into the polymer. For example: Ethylene oxide polymerization is initiated by the addition of poly ε,N-carbobenzoxy-L-lysine, which leads to PEG-copoly ε,N-carbobenzoxy-L-lysine.

C. Incorporation of a Degradative or Cleavage Component, C, into the Polymer The time of residence of the polymer on the tissue and the ability of the host to clear the polymer may be enhanced by incorporating sequences which are non-enzymatically degradable.

1. For Degradation at Bristles by Addition of a C Component

C can be added to the polymeric material so that the "bristles" are released from the backbone when the C component degrades. For example, monomethoxy PEG reacts with d,l-lactide (1:3 molar ratio) in xylene in the presence of stannous octate under reflux for sixteen hours to yield a PEG with an end group which degrades over time in water. The hydroxyl at the terminus of the trilactide end group is activated with CDI, which is then further reacted with PLL by methods presented above to yield an (A)xC-b-(B)y, an (A)xC-(B)y or an (A)xC-(B)y-C(A)z copolymer.

2. Incorporation of C into the Backbone for Enzymatic Degradation of the Backbone Certain amino acid sequences are recognized by specific proteolytic enzymes. These may be incorporated into a polyoeptide backbone. For example, by solid phase methods, a peptide is produced which contains six lysines, followed by the sequence proline-X-glycine-proline, where X is any neutral amino acid, and repeated three times to obtain a peptide with 30 residues. The sequence proline-X-glycine-proline is hydrolysed by the enzyme collagenase. The peptide is reacted with CDI mono-activated PEG to yield an (A)x-b-C(B)y, an (A)x-C(B)y or an (A)x-C(B)yC-(A)z copolymer which is enzymatically degradable.

D. Synthesis of a Polymeric Material Using a Component that Changes From One Function to a Second Function Over Time

1. Synthesis of a Polymeric Material Using a B Component that Converts from a Binding Component to a Non-binding Component D The duration of binding of a polymeric material can be controlled by synthesis of a polymeric material with a non-binding backbone which is converted to a binding backbone through degradable linkages. For example, terminal amine polyglutamic acid is reacted with CDI PEG to produce an (A)x(D)y-b-(B)y copolymer. The copolymer is dissolved in water at pH 2 and lyophilized to convert the carboxylic acid salt to the free acid. The polymer is dissolved in DMF, and the glutamic acid residues are activated with TSU. The activated polymer is then reacted with boc protected aminoethanol in DMF overnight at room temperature and then deprotected and desalted. The product is initially polycationic and binding, but hydrolyses to a non-binding polyanion.

2. Synthesis of a Polymeric Material Using an A Component that Converts from Repelling Tissue to One which does not Repel or Bind to Tissue A polypeptide may be reacted with an (unprotected) hydroxy acid using peptide synthesis techniques to yield a nonionic polymer. Over time, this amide linkage degrades, and the nonion converts from repulsive to not repulsive. For example, using solid phase synthesis, a peptide is produced in which the first twenty residues are lysines, the next ten residues are arginine, and the next twenty residues are lysines. The peptide is fully deprotected, and is then reacted with lactic acid, 1-ethyl-3-(3-dimethylaminopropyl)carbodiimide (EDC), and N-hydroxysulfosuccinimide in buffered water at pH 9, yielding an (A)x-(B)y-(A)z copolymer in which the "A" segment is originally nonionic, but upon degradation becomes ionic.

E. Addition of Bioactive Components to the Polymeric Material

Some interactions of tissues with the polymer may be desirable. A variety of mechanisms can be used to effect this result, including cell specific peptide sequences that can be used to target the polymer to bind only to certain cell types, or to attract or inhibit binding of soluble mediators, including enzymes.

1. Incorporation of Cell Specific Peptide Sequences

Cell specific peptide sequences can be incorporated into the copolymer as follows. The peptide tyrosine-isoleucine-glycine-serine-arginine (YIGSR) is fully protected with the exception of the carboxyl terminus, and is activated with 2-(1H-Benzotriazol-1-yl)-1,1,3,3-tetramethyluronium hexafluorophosphate (HBTU). This is then reacted with mono-amino PEG in DMF, giving α-hydroxy, ω-YIGSR PEG. This compound is CDI activated in DMF, reacted with PLL in DMF, followed by deprotection of YIGSR in DMF, yielding a copolymer with a pendant bioactive agent.

2. Derivatization of PEG with an Amino Acid

The derivitization of PEG with an amino acid makes it suitable for inclusion into a polypeptide using solid phase techniques. For example, CDI mono-activated PEG is reacted with α-Fmoc protected lysine, forming ε-lysine-PEG. Using solid phase techniques, a copolymer is made of lysines and ε-lysine-PEGs, using the method of Atassi, M. Z., Manshouri, T., "Synthesis of Tolerogenic Monomethoxy-polyethylene Glycol and Polyvinyl Alcohol Conjugates of Peptides" *J. Prot. Chem.*, 10, 623-/ (1991), the teachings of which are incorporated herein.

III. Medical Applications of Polymers

As described above, the bi-functional polymers have a variety of applications. Several are demonstrated in detail in the following examples. These include local application, either at the time of surgery or via injection into tissue, to prevent adhesion of tissues; to deliver bioactive compounds where release is effected more efficiently or at a more desirable rate or where tissue encapsulation could detrimentally effect or delay release; prevention of thrombus formation at blood vessel surfaces, particularly following angioplasty; alteration of attachment of cells, especially to prevent attachment of cells, and therefore decrease metastasis of tumor cells; and as coatings on prosthetic implants such as heart valves and vascular grafts derived from processed tissues.

As defined herein, "tissue" includes cells, cell aggregates, tissues removed from the body, and tissues present in the body. This term can also be applied to treated tissue, such as tissue heart valves, blood vessels and membranes, where the tissue is no longer living and has been chemically fixed, or a cryopreserved blood vessel or other tissue.

The polymeric materials can be applied directly by localized or topical application, or if targeted as described herein, systemically. Topical or localized application is achieved generally by spraying or injecting a very thin layer (usually on the order of monolayers of polymeric material) onto the tissue surface to which adhesion is desired. Methods for applying the polymeric materials in this manner are known to those skilled in the art.

As described below in the examples, these polymeric materials have been applied in three systems where the prevention of cell and tissue contact is desirable.

1. Damage to the surface of organs during surgery may cause adherence of tissues which are in close contact. This problem is particularly severe in reproductive surgery, where extensive adhesion formation may cause infertility. In a surgical model in rats, an injury was made to the uterine horns, followed by treatment with PEG-b-PLL. Adhesions were reduced from an extent of 78% for control (treated with HEPES-buffered saline, the vehicle) to 9% for treatment with a 1% concentration of the polymeric material by peritoneal lavage.

2. After balloon angioplasty, damage to the endothelium may lead to thrombus formation, due to the interaction of platelets with the vessel wall. Moreover, thrombosis may lead to restenosis. In rats, an injury was made to the carotid artery, followed by treatment with PEG-b-PLL. Thrombosis was completely blocked by exposure to a 5% concentration of the polymeric material prior to resumption of blood contact.

3. During laparoscopic removal of tumors, tumor cells may be released into the pelvic cavity, and the tumor cells may metastasize. Tumor cells were incubated with PEG-b-PLL, and then seeded intraperitoneally in mice. Implantation of tumor cells upon the injured tissue surfaces was reduced from 0.93 g in controls to 0.17 g in treated animals.

There are a number of other medical applications for the polymeric materials described herein.

1. Thrombosis upon injured vascular surfaces may cause complications in vascular surgery. This is especially true in microvascular surgery, where thrombosis at the ends of the vessels at the anastomosis may lead to occlusion. Prior to anastomosis, the ends of the vessels to be joined are dipped in a 1% solution of PLL-b-PEG, or a similar bi-functional polymeric material, to pacify the injured vessel surfaces. Thrombosis may thus be reduced, and vessel patency may be improved.

2. Cardiovascular implants are adversely affected by thrombosis, platelet attachment and aggregation. As an example, thrombosis upon the surfaces of heart valve implants made from human or animal tissues processed, for example, by cryopreservation, lyophilization or chemical fixation, is implicated in acting as a nidus for calcification. Thus, thrombosis may lead to long-term valve failure by calcification of the valve to materials. Tissue heart valves are placed in a 2% solution of PEG-b-PLL, or a similar bifunctional polymeric material, in buffered saline at 4° C. for 1 hour. The valve is then rinsed in saline for 5 minutes and packaged for implantation later. During the incubation in the polymeric material solution, the bi-functional polymeric material adsorbs by its binding domain, thus immobilizing the non-binding domain in the processed tissue valve. This subsequently blocks thrombosis after implantation, and long-term calcification at the sites of thrombosis may thus be reduced.

3. The adhesion of immune cells to the vascular surface of a transplanted organ is one of the causes of acute organ-rejection. This acute rejection may be related to an acute inflammatory reaction, in which white blood cells adhere to the vascular surface of the transplanted organ. Hearts for transplantation are placed in a preservation medium containing added bi-domain polymeric material, such as PEG-b-PLL. The organ is stored in the medium, e.g., at 4° C., until transplantation. During the storage period, the bifunctional polymeric material adsorbs to the vascular surface of the organ, which subsequently blocks the adhesion of immune cells to the organ after transplantation. This may reduce acute rejection of the organ.

4. In many cases, it may be advantageous to have a drug that is immobilized upon and or released from a surface. An example is the fibrinolytic enzyme streptokinase (SK). Streptokinase is considered inferior to tissue plasminogen activator (tPA) because tPA binds to fibrin and exerts its fibrinolytic activity in an immobilized manner. SK exhibits no such binding. This difficulty can be eliminated by binding of the enzyme to the polymeric material described herein. SK is attached to the ends of the non-binding domains which are connected to a binding domain. In this case, since the bioactive group is rather large, being an enzyme, a fewer number of nonbinding domains is optimal, as is a larger binding domain. The SK-grafted bi-domain polymeric material, e.g., SK-grafted PEG-PLL AB block copolymer, is administered locally to the site of balloon angioplasty using a catheter, such as a balloon catheter that weeps fluid. The SK-PEG-PLL binds to the vessel surface, yielding a localized and more sustained fibrinolytic activity exactly at the site of its application.

The same technology can be applied using any of numerous other classes of drugs, such as growth factors, growth factor antagonists, receptor antagonists, adhesion factors, adhesion antagonists, antimitotics, antisense oligonucleotides, and many others. In a similar approach, the drug is attached to the ends of the nonbinding domain via a cleavable linker, such as a lactic acid dimer or oligomer, or an enzymatically cleavable peptide or saccharide. In this way, a controlled release of the tissue-bound drug may be engineered into the conjugate of the drug with the bi-functional polymer.

5. In vascular injury, such as occurs when a diseased coronary artery is injured by balloon angioplasty, the endothelial monolayer that protects the vessel wall from contact with blood is removed. Thrombosis follows due to blodd platelet binding to proteins in the injured vessel wall. This interaction can be blocked using bi-functional polymeric materials, such as poly(N-vinyl pyrrolidinone)-chitosan block copolymers, abbreviated PVP-chitosan. The ratio of the PVP to chitosan, and the molecular configuration of the PVP-chitosan, which is dependent on the number of PVP per chitosan, may be optimized to resist substantially all adhesion of blood cells to the vessel wall. This blocks thrombosis, which is suspected to cause further vessel disease such as restenosis. It may also slow the process of reendothelialization. A bioadhesive domain may be attached to the ends of the nonbinding domains, and this bioadhesive domain may be selected to bind to endothelial cells and support their adhesion but not to blood platelets so as to support thrombosis. The laminin pentapeptide tyr-ile-gly-ser-arg (YIGSR) is attached via its N-terminal primary amine to end-groups on the PVP-chitosan AB block copolymer. After adsorption, the nonbinding groups block thrombosis, but the YIGSR peptide on the termini of the nonbinding groups support the attachment and migration of endothelial cells from the noninjured periphery of the blood vessel. This may thus accelerate vascular healing and permit reendothelialization of the injured zone without contact of the artery with blood. Such approaches may be carried out on numerous other tissues, e.g., a demesothelialized surface to accelerate peritoneal healing and prevent adhesions, and a deepithelialized cornea to accelerate healing after corneal abrasion, among others.

6. In some cases the binding domain may be highly specific in nature, rather than nonspecific as with exclusively polycationic binding domains. For example, a water-soluble polymer that is nonionic, such as poly(vinyl alcohol) (PVA), may be grafted to a receptor antagonist, such as a receptor antagonist that binds to adhesion receptors on cell surfaces. For example, a PEG-PVA AB block copolymer is synthesized. Subsequently, several sialyl Lewis-X (LeX) oligosaccharides are attached to the multiple alcohols on the PVA chain. This PEG-Lex-PVA copolymer is administered by injection into the blood stream. The polymeric material binds to the surfaces of cells expressing E-selectin, which binds to LeX. Since there are several LeX oligosaccharides bound to the PVA domain, binding to E-selectin on cell surfaces is quite strong. Thus, the LeX PVA domain serves as the binding domain, and the PEG domain serves as the nonbinding domain. The net effect may thus be to block the adhesion of cells via numerous receptors by immobilizing a nonbinding domain such as PEG to the surface of the cell.

IV. Optimization of the Polymeric Material for Individual Applications

The biological performance of these materials is optimized by altering the structure of the polymers, the ratio of the number of tissue-binding polymers to non-binding polymers, and the ratio of the mass of the tissue-binding polymers to non-binding polymers.

In some case, polymeric materials exhibiting more than one manner of degradation may be required to achieve different results. For example, degradation by nonenzymatic hydrolysis will depend primarily upon the accessibility of the polymeric material to water and the local pH. Given that pH and water concentration are similar throughout many parts of the body, such a mode of degradation would yield a loss in repulsiveness that depends mostly upon time. As another example, if the degradable region was sensitive to an enzyme, the activity of which was not highly regulated but rather was present in the body fluids at a more or less constant level, the rate of loss of repulsiveness would again depend primarily upon time. As another example, if the degradable region was sensitive to an enzyme, the activity of which was more highly regulated, the rate of loss of repulsiveness would then depend more upon the expression of that particular enzyme activity. For example, many types of cells express the proteases plasmin or collagenase during migration. A sensitivity to plasmin would then cause all migrating cells to degrade the repulsiveness of the polymeric material and thus attach. This might be useful, e.g., in protecting an injured vessel wall from blood platelets, but permitting an endothelial cell migrating from a noninjured region of the vessel wall to migrate over the treated area, degrading its nonadhesiveness as it did so and permitting the endothelial cell to attach to the vessel wall and migrate over it. This could permit reendothelialization of a de-endothelialized vessel wall without ever permitting direct contact of the endothelial cell-free surface with blood platelets.

The biological performance of these polymeric materials depends upon their structure. Specific features of biological performance include binding to the tissue, repulsion of opposing tissues, duration of binding to the tissue, duration of repulsion of opposing tissues, and the mode of loss of binding or repulsion. Specific features of polymeric material structure include the type (chemical composition) of tissue-binding domain, type of non-binding domain, the ratio of the mass of binding to non-binding domains, the number of binding to non-binding domains, the inclusion of sites that are particularly susceptible to nonenzymatic hydrolysis, the inclusion of sites that are particularly susceptible to enzymatic hydrolysis, and the inclusions of sites with particular biological affinity.

A variety of ways can be utilized to optimize the desired properties. For example, when a PEG-b-PLL brush copolymer is used to protect an injured tissue surface from the adhesion of cells approaching from the fluid phase in contact with that tissue surface, the polymeric material can be made more desirable by studies conducted using a tissue culture model, such as cell adhesion to gelatin coated surfaces in tissue culture medium containing 20% serum. Gelatin is coated upon the multiwell dishes using standard tissue culture technique, for example, from a 3% gelatin solution. A 30 minute exposure to medium with 20% serum will lead to the adsorption of fibronectin, a protein leading to cell adhesion, to the gelatin surface. If fibroblasts are seeded on this surface in medium containing 20% serum, rapid adhesion and spreading will occur. A measurement of the fraction of cells adhering (Fa) and fraction of cells spreading (Fs) may be made based on morphological criteria using light microscopy. Such measurements conducted 4 hours following seeding provide useful measures of adhesion and repulsion. A family of PEG-b-PLL polymeric materials are synthesized, e.g., according to the following schedule:

| MW of PLL | MW of PEG | Fraction of lysine residues grafted with a PEG chain |
|---|---|---|
| 1000 | 1000 | 1/50 |
| 1000 | 1000 | 1/10 |
| 1000 | 1000 | 1/5 |
| 10000 | 1000 | 1/50 |
| 10000 | 1000 | 1/10 |
| 10000 | 1000 | 1/5 |
| 10000 | 5000 | 1/50 |
| 10000 | 5000 | 1/10 |
| 10000 | 5000 | 1/5 |
| 10000 | 10000 | 1/50 |
| 10000 | 10000 | 1/10 |
| 10000 | 10000 | 1/5 |
| 20000 | 5000 | 1/50 |
| 10000 | 5000 | 1/10 |
| 20000 | 5000 | 1/5 |
| 20000 | 10000 | 1/50 |
| 20000 | 10000 | 1/10 |
| 20000 | 10000 | 1/5 |

For each polymeric material composition, Fa and Fb are measured at 4 hours. Polymeric materials with very low ratio of PEG to PLL, such as the polymeric material with 20000 Da PLL, 5000 Da PEG, with 1/50 of the lysine residues grafted with a PEG chain, would be expected to be relatively ineffective in prevention of fibroblast attachment and spreading.

In the case where a brush copolymer which desorbs slowly from tissue is desirable, the same assay system could be used, and polymeric materials could be synthesized with other binding domains, such as in the schedule below:

| Binding domain composition | MW of binding domain | MW of PEG | Fraction of binding residues grafted with a PEG chain |
|---|---|---|---|
| Poly L lysine | 20000 Da | 50000 Da | 1/10 |
| Poly L histidine | 20000 | 5000 | 1/10 |
| Poly L arginine | 20000 | 5000 | 1/10 |
| Poly L ornithine | 20000 | 5000 | 1/10 |
| Poly ethyleneimine | 20000 | 5000 | 1/10 |
| Poly amino ethylacrylate | 20000 | 5000 | 1/10 |
| Chitosan | 20000 | 5000 | 1/10 |

By varying the specific nature of the charge, in this example used to obtain binding to tissues, the rate of desorption may be adjusted. In the assay system, cells could be seeded once each day on a gelatin surface variously treated, and Fa and Fs measured the 4th hour after seeding.

Afterwards, the substrates could be rinsed with medium and stored in tissue culture with medium for examination after the next day. Subsequent measurements over many weeks would permit the rate of loss of cell repulsiveness to be determined for each formulation.

In the situation where an AB block copolymer was to be used to prevent thrombosis and intimal thickening upon an artery surface injured by balloon angioplasty, after initial experimentation as described above to determine a desirable ratio of binding domain to non-binding domain, and a desirable optimal composition of the binding and non-binding domains, animal experimentation could be performed. For example, if the above experimentation yielded good repulsion for 14 days with PLL of degree of polymerization (DP) 30 and a PEG of DP 150, animal experimentation could be performed making small excursions about this formulation, for example by the following schedule:

| PLL DP | PEG DP |
|---|---|
| 20 | 100 |
| 30 | 100 |
| 40 | 100 |
| 20 | 150 |
| 30 | 150 |
| 40 | 150 |
| 20 | 200 |
| 30 | 200 |
| 40 | 200 |

Thrombosis could be measured at 24 hours following injury and treatment, and intimal thickening could be measured at 28 days following injury and treatment, using light microscopy with histological staining with Gomori's trichrome staining for the measurement of thrombosis and Verhoeff's staining for the measurement of intimal thickening.

If it were desired to further optimize, for example based on the nature of the binding domain, an optimal formulation from the above schedule could be selected, and the PLL domain could be replaced with poly(L-histidine), poly(L-arginine), poly(L-ornithine), polyethyleneimine, poly(aminoethylacrylate), and chitosan, with guidance from the experimentation in vitro.

If it were desired to further optimize based on the rate of degradation of the binding domain, an optimal formulation from the above schedule could be selected and the poly(L-amino acid) binding domain could be replaced with a poly(D-amino acid) domain of the same amino acid, for example poly(D-lysine) for poly(L-lysine). Each polyamino acid would be expected to exhibit different stability to proteolysis in vivo.

If it were desired to even further optimize based on the rate of degradation of the binding domain, an optimal formulation from the above schedule could be selected and a protease sensitive site could be placed between the binding and the non-binding domains. For example, many cells express proteases on their leading edge as they migrate, such as plasmin, collagenase, or elastase. By appropriate selection of a protease sensitive site it should be possible to design a polymeric material that is sensitive to endothelial migration, permitting the polymeric material to prevent thrombosis, but also permitting the polymeric material to be degraded by endothelial cells repopulating the vessel surface as healing and reendothelialization occurs.

A similar outcome may be obtained by placing adhesion peptides at the termini of the non-binding domains. For example, the laminin peptide tyr-ile-gly-ser-arg is known to support endothelial cell adhesion and spreading. However, platelets do not bind avidly to this sequence. It is thus possible to synthesize an AB block copolymer with the adhesion peptide on the termini, or elsewhere, on the non-binding domain. This may also permit the prevention of platelet contact while at the same time permitting endothelial cells to migrate over the injured vessel zone to repopulate and reendothelialize the injured zone.

An AB block copolymer can be used to immobilize a drug upon a tissue surface. For example, the formation of fibrin is known to be involved in the formation of postoperative adhesions, and fibrinolytic proteins have been shown to be effective in reducing adhesion formation. More expensive fibrinolytic proteins such as tissue plasminogen activator (tPA) have advantages over less expensive ones such as streptokinase (SK) in that the tPA binds to the tissue surface at sites of fibrin. This retention of tPA by immobilization is an important benefit. This retention may be mimicked, however, by attaching the SK to a bi-domain polymeric material. For example, a family of AB block copolymer could be synthesized according to the following schedule:

| DP of PLL | DP of PEG | Presence of SK |
|---|---|---|
| 25 | 100 | Yes |
| 50 | 100 | Yes |
| 100 | 100 | Yes |
| 25 | 500 | Yes |
| 50 | 500 | Yes |
| 100 | 500 | Yes |

These polymeric materials could be evaluated for the ability to prevent postoperative adhesion in rats after devascularization injury of the uterine horn, each delivered as a 1% solution in buffered saline. After selection of an optimal formation, the equivalent polymeric material could be synthesized with albumin, an inactive protein, rather than SK to serve as a control.

The present invention will be further understood by reference to the following non-limiting examples.

EXAMPLE 1

Synthesis and Characterization of PEG-b-PLL

Materials and Methods

PEG-b-PLL Synthesis

Poly(ethylene glycol) was grafted to poly(L-lysine) based on the calculations of Sawhney and Hubbell, "Poly(ethylene oxide)-graft-poly(L-lysine) copolymers to enhance the biocompatibility of poly(L-lysine)alginate microcapsule membranes" *Biomaterials* 13:863–870 (1992), and on the chemistry of Beauchamp, et al., "A new procedure for the synthesis of polyethylene glycol-protein aducts: the effects on function, receptor recognition, and clearance of superoxide dismutase, lactoferrin, and alpha 2 macroglobulin" *Anal. Biochem.* 131:25–33 (1983), the teachings of which are incorporated herein. Monomethoxy terminated poly(ethylene glycol((PEG) (20 g, mol. wt. 5000; Aldrich, Milwaukee, Wis., USA) was dried by azeotropic distillation from benzene, and precipitated by addition to anhydrous diethyl ether. The polymer was dried overnight under vacuum, and stored under argon. The terminal hydroxyl on the PEG was then activated with 1,1-carbonyldiimidazole (CDI; Sigma, St. Louis, Mo.). Under argon, CDI (0.194 g) was weighed out, then added to dry PEG (10 g) in anhydrous dichloromethane. The reactants were stirred under argon at room temperature for two hours, and the product was then precipitated by addition to anhydrous ether. The product was dried under vacuum overnight.

Poly(L-lysine) (PLL) (1 g, mol. wt. 21,400; Sigma) was dissolved in 25 ml of 50 mM sodium borate buffer (pH 9) and filter sterilized three times through 0.2 µm syringe filters (Nalgene, Rochester, N.Y.) to remove microbial contamination. In a sterile reaction bulb and in a sterile cabinet, CDI activated PEG (CDI-PEG) (6.6 g) was added to the poly(L-lysine) solution with vigorous stirring for one day. The solution was then dialyzed (SpectraPor™ dialysis tubing, MW cutoff 12,000–14,000; Spectrum Medical Industries, Los Angeles, Calif.) against four liters of phosphate buffered saline (pH 7.4) for one day. The solution was then freeze dried, yielding 3.44 g of product.

NMR Analysis of PEG-b-PLL $^1$H NMR analysis of PEG-b-PLL was performed in $D_2O$ on a 500 MHz General Electric instrument.

Results $^1$H NMR analysis of PEG-b-PLL in $D_2O$ indicated the presence of new peaks which were not present in the individual spectra of PLL or PEO. These peaks corresponded to the conversion of some epsilon amines on the PLL. The new peaks were presumably due to the addition of PEG to the PLL. Analysis of the peak at 2.9 ppm, corresponding to the protons on the delta carbon on the PLL side chain, and a smaller peak at 3.0 ppm, corresponding to the protons on delta carbons of side chains which had reacted with CDI-PEG, indicated that 5.73% of the lysyl residues had reacted with CDI-PEG. This corresponds to 9.57 PEG chains per PLL chain, or an average molecular weight of PEG-b-PLL of 69,250 Daltons. Comparison of the peaks at 2.9 ppm and 3.0 ppm with the peak at 3.3 ppm, resulting from the monomethoxy group on the PEG, indicated that only 19.3% of the PEG in the product was actually attached to the PLL. This was due to incomplete dialysis of the product, however, the presence of the PEG could be accounted for in the experiments by the choice of appropriate controls.

EXAMPLE 2

Effect of PEG-b-PLL on Cell Spreading Monomethoxy PEG off on One Capped End in Vitro Materials and Methods Human foreskin fibroblasts (HFFs) were incubated in DMEM containing 10% fetal bovine serum (FBS) with 0.2% PEG-b-PLL (as described in Example 1), PLL or PEG for five minutes, and were then seeded into 24 well dishes which also contained DMEM with 10% FBS and 0.2% (w/v) of the appropriate polymer. The fibroblasts were seeded at 2000, 10,000, 25,000 or 40,000 cells/cm$^2$, with two replicates at each concentration. At three hours post seeding, the number of well spread cells and the number of total cells was counted at 200× on a Nikon phase contrast inverted microscope, two fields per well, and the percentage of cells which were well spread was calculated.

Results

The percentage of spread cells (spread cells/total cells × 100) is an indication of seeding efficiency. Seeding efficiency will remain relatively constant regardless of concentration of cells within the range of cell concentrations studied here However, a polymer which prevents spreading at low concentrations may be ineffective at higher concentrations. Thus, it is logical to examine a range of cell seeding concentrations.

TABLE 1

| | Prevention of Fibroblast Spreading | | | |
|---|---|---|---|---|
| | concentration of cells (cells/cm$^2$) | | | |
| polymer | 2000 | 10,000 | 25,000 | 40,000 |
| | % spread cells; std. dev. | | | |
| control | 50.8 ± 18.4 | 37.5 ± .71 | 39.5 ± 9.19 | 59.0 ± 5.66 |
| MPEG | 33.8 ± 26.9 | 56.0 ± 1.41 | 59.5 ± 12.0 | 62.5 ± .71 |
| PLL | 5.75 ± 7.22 | 23.5 ± 7.78 | 27.5 ± 3.54 | 41.0 ± 1.41 |
| PEG-b-PLL | 0.0 ± 0.0 | 1.0 ± 1.41 | 0.5 ± .71 | 1.5 ± .71 |

PLL seems to inhibit spreading somewhat of HFF's at low cell concentrations, however, at higher seeding concentrations, PLL allowed cell spreading. PEG-b-PLL strongly inhibited fibroblast spreading at all concentrations tested.

EXAMPLE 3

In Vivo Study of the Use of PEG-b-PLL to Prevent Pelvic Adhesions

Materials and Methods

PEG-b-PLL (as described in Example 1) was tested at a 1% concentration in 10 mM HEPES buffered saline. From gravimetric analysis, it was estimated that PEG-b-PLL was 20% PLL by weight. Thus, 0.2% PLL and 0.8% PEG were mixed together in 10 mM HEPES buffered saline as a control, referred to as the PLL+PEG control. To control for the individual effects of PLL and PEG, a 0.2% solution of PLL, referred to as the PLL control, and a 0.8% solution of PEG, referred to as the PEG control, were prepared, both in 10 mM HEPES buffered saline. HEPES buffered saline alone was also tested, referred to as the HEPES control.

The polymer solutions were prepared as follows: The 10 mM HEPES buffered saline was first autoclaved and then filter sterilized (150 ml disposable filter system, Corning, Corning, N.Y.) before addition to polymers. Polymer solutions were shaken until dissolved, and then syringe filter sterilized as above. The solutions containing PLL, however, were filter sterilized four times to assure removal of microbial contamination. The polymer solutions looked identical, and were labeled by a code to assure that the surgeries would be performed blind.

Controlled injuries to the uterine horn in 14 week old rats were made by electrocautery to devascularize the horns and produce serosal injury on the antimesenteric surfaces. Seven days after surgery, the animals were sacrificed and the horns were examined. The portion of the horn which was judged to be adhered to mesentery or rectum was measured with a ruler, and compared to the total length of the horn. This "percent adhesion" refers to the length of the horn which displayed adhesions compared to the total length of the horn. In each animal, the "percent adhesion" values were averaged between the two horns. This average value was considered to be one data point.

The uterine horns were judged to be free of adhesions (grade 0), containing filmy adhesions (grade 1) or containing severe adhesions (grade 2). If only a portion of an adhesion was found to be grade 2, the length of the grade 2 area was measured, and compared to the length of the adhesion which was grade 1. It was thus possible to score a horn with an intermediary value between grade 1 and grade 2. The grade of adhesions in the animals were averaged between the two horns.

Data for percent adhesion of horn was analyzed using a one factor analysis of variance. Data for severity of adhesions was analyzed using the distribution free, non-parametric Kruskal-Wallis test.

Results

The extent of adhesions as assessed seven days after uterine horn injury is presented in Table 2.

TABLE 2

| | Extent of Adhesions | | |
|---|---|---|---|
| Treatment | ave. % adhesion | Std. Dev. | Count |
| HEPES | 77.9 | 6.62 | 7 |
| MPEG | 34.4 | 3.77 | 6 |
| PLL | 26.0 | 4.76 | 7 |
| PEG + PLL | 20.3 | 8.10 | 7 |
| PEG-b-PLL | 8.79 | 4.09 | 7 |

All treatments differ significantly from other treatments at 95% by the Fisher PLSD post-hoc test, except for PLL versus PEG+PLL, which did not differ significantly.

The extent of adhesions was reduced by the application of PEG, PLL or PEG-b-PLL as compared to the HEPES alone control. The combination of PEG plus PLL did not differ significantly from PLL alone. The PEG-b-PLL treatment was significantly different from the PEG+PLL treatment.

The severity of adhesions was also assessed and is presented in Table 3. The data gathered concerning the grade of the adhesions was parametric, but not normally distributed. The average grade was calculated, and is indicative of the severity of the adhesions. The standard deviation is useful to judge the reproducibility of the data, despite the lack of statistical meaning due to the non-normal distribution. The data was analyzed using a rank sum type test. The rank sum from each treatment was divided by the number of samples in the treatment, yielding the mean rank.

TABLE 3

| | Severity of Adhesions | | |
|---|---|---|---|
| Treatment | ave. grade | std. dev. | mean rank |
| HEPES | 1.57 | .45 | 26.7 |
| PEG | 1.08 | .20 | 17.0 |
| PLL | 1.03 | .07 | 16.1 |
| PLL + PEG | 1.07 | .19 | 16.6 |
| PEG-b-PLL | .821 | .31 | 10.9 |

The Kruskal-Wallis test suggested a statistical difference between treatments, with p=0.0128 H(corrected for ties)= 12.71.

EXAMPLE 4

In Vivo Study: Prevention of Thrombosis Following Artery Crush Using PEG-b-PLL Materials and Methods Male Sprague-Dawley rats weighing 350–400 g were used in this study. The animals were anaesthetized with pentobarbital (50 mg/kg body weight). Xylocaine was administered subcutaneously in the region of the surgical manipulations just prior to incision. The carotid artery was exposed by careful dissection 1 cm. beyond the external carotid branch point. Atraumatic arterial clips were used to clamp off the artery at the most proximal exposed point of the internal and external carotid branches and at the most distal exposed point of the common carotid. PE50 polyethylene tubing attached to a 30 gauge needle was introduced into the internal carotid. Residual blood was rinsed from the artery using HEPES buffered saline. The common carotid was crushed with hemostats to induce an injury to the arterial wall. The artery was then filled with a sterile 5% solution of PEG-b-PLL (as described in Example 1) in HEPES buffered saline. The solution remained in the vessel for two minutes and then was withdrawn through the tubing. The tubing was removed, and the internal carotid was tied off with 5-0 silk suture. The arterial clips were then removed to allow blood flow. The muscular layer of the incision was closed with continuous 3-0 Vicryl suture, and the skin was closed with 9 mm staples. Animals were sacrificed at either two hours or twenty-four hours post-surgery. The vessels were excised, rinsed, and fixed in buffered formalin. At least twelve hours later, the vessels were dehydrated in a graded ethanol series, exchanged with xylene, embedded in paraffin, sectioned to a thickness of 5 μm, and mounted on glass slides. Staining was by Masson's trichrome.

Results

As expected in the case of an arterial wall injury, all control animals displayed significant thrombosis formation, both at the two and twenty-four hour time points. Application of the PEG-b-PLL solution prevented thrombosis at both time points. All treated arteries were completely patent, allowing normal blood flow through the carotid artery (at 2 hour time point, n=2 treatment, n=2 control; at 24 hour time point, n=3 treatment, n=2 control; figures shown are typical of all n for that condition).

Figure 1:
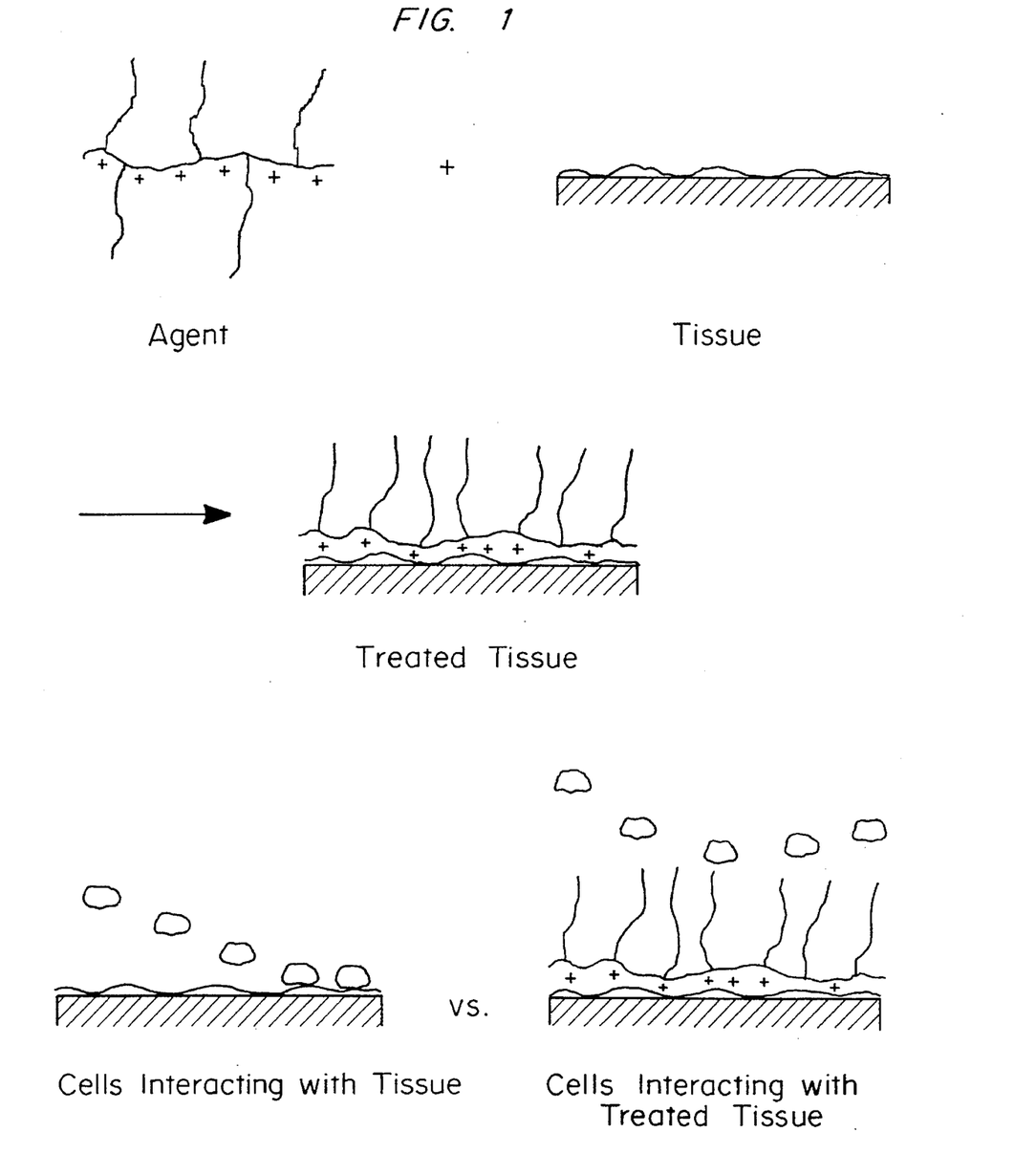
FIG. 1 is a schematic illustration of the interaction between a two domain polymeric material and cells or tissue which has been treated with the polymeric material to decrease adhesiveness.
Figure 2A:
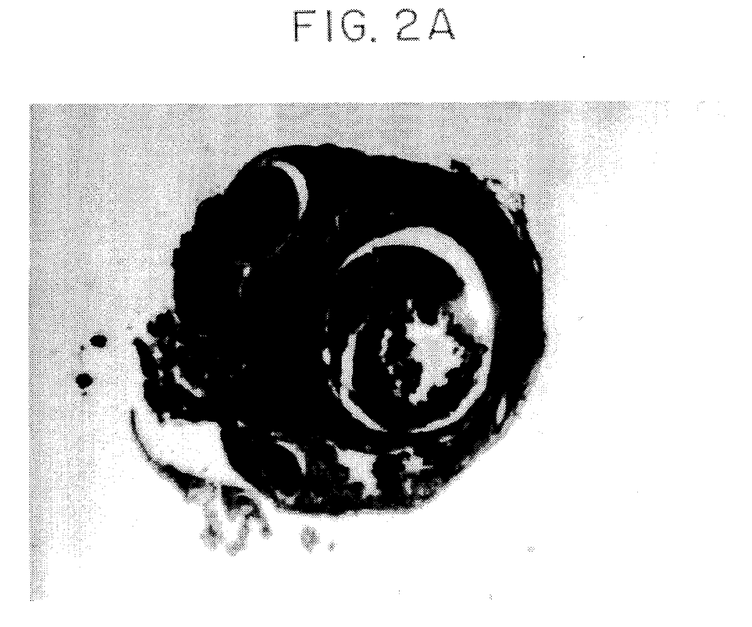
FIGS. 2a and 2b are photographs of a rat carotid artery 24 hours after crush injury without treatment (FIG. 2a) and treated with a 5% solution of PEG-b-PLL for two minutes (FIG. 2b).
Figure 2B:
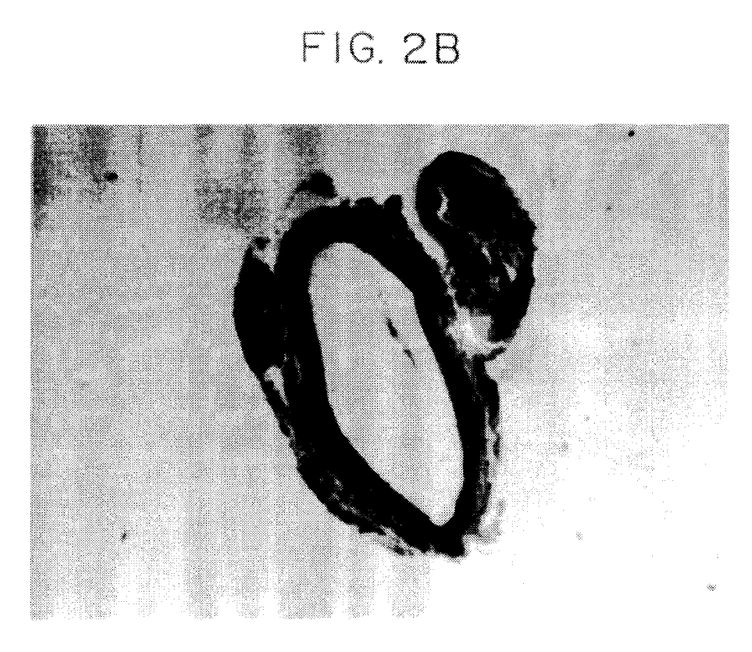

FIGS. 2a and 2b are photographs at a magnification of 600 fold of the rat carotid artery 24 hours after crush injury without treatment (FIG. 2a) and treated with a 5% solution of PEG-b-PLL for two minutes (FIG. 2b). There were no signs of adverse tissue response to bi-functional polymer.

EXAMPLE 5

Effect of PEG-b-PLL Addition on Tumor Cell Seeding In Vivo

Materials and Methods

A model of laproscopic surgery was performed. A 16 gauge angiocatheter was inserted intraperitoneally in male C3H mice, and insufflated with 5 ml of air. Three treatments were performed, with 18 animals per treatment. Treatment 1 consisted of the injection of $1\times10^6$ tumor cells in one ml of phosphate buffered saline. Treatment 2 consisted of injection of $1\times10^6$ tumor cells in one ml of phosphate buffered saline containing 0.1% PLL-b-PEG. Treatment 3 consisted of the injection of $1\times10^6$ tumor cells in one ml of phosphate buffered saline containing 1% PLL-b-PEG. After sixteen days, the tumor volume was compared at the trocar site, as well as at all other sites.

Results

The results are presented in Table 4. Application of PLL-b-PEG reduced tumor volume significantly ($p<0.05$). The differences between 0.1% and 1% PLL b PEG were not significant.

TABLE 4

| | Tumor Volume at 16 days | |
|---|---|---|
| Treatment | Trocar Site (g) | All Other Sites (g) |
| control | .485 | .929 |
| .1% PLL-b-PEG | .179 | .297 |
| 1% PLL-b-PEG | .160 | .173 |

EXAMPLE 6

Synthesis of Methacrylic PEG Copolymerized with Aminoethyl Methacrylate

Monomethoxy PEG was reacted with methacryloyl chloride under anhydrous conditions, producing methacrylic PEG. This was copolymerized with aminoethyl methacrylate (AEMA), to yield 85 AEMA:15 methacrylic PEG. The product was then dialyzed against water using the method of U.S. Pat. No. 5,075,400 to Andrade, et al. "Polymer supersurfactants for protein resistance and protein removal".

EXAMPLE 7

Evaluation of AEMA/Methacrylic PEG Copolymer In Vitro

Human foreskin fibroblasts were trypsinized and seeded in complete media containing 0.2% (w/v) AEMA/methacrylic PEG copolymer. Cells were seeded on polystyrene culture dishes at a concentration of 2000, 15,000, 30,000 cells/cm$^2$.

TABLE 5

| | Concentration of Spread Cells 3 hour post-seeding. | | |
|---|---|---|---|
| | concentration of cells (cells/cm$^2$) | | |
| treatment | 2000 | 15,000 | 30,000 |
| AEMA copolym. | 0 | 0 | 0 |
| none | 212 | >1000 | >1000 |

The results demonstrate the effectiveness of the polymer in preventing attachment and growth of the treated cells, especially as compared with the control cells.

Modifications and variations of the methods and compositions described herein will be obvious to those skilled in the art from the foregoing detailed description. Such modifications and variations are intended to come within the scope of the appended claims.

We claim:

1. A method for modifying cell contact with a surface, comprising applying to the surface a biocompatible polymeric material which is selected from the group consisting of copolymers having the formulas (A)x(B)y; (A)x(B)y(A)z; (B)x(A)y(B)z; and a brush copolymer (A)x(B)y having bristles of poly(A);

wherein (A)x, (A)y and (A)z are biocompatible synthetic polymers and mixtures of polymers that form a region which is polynonionic at a pH of between 6.5 and 8.5 and does not bind tissue; and wherein (B)y, (B)x, and (B)z are biocompatible, water-soluble synthetic polymers or mixture of polymers that form a region which is polycationic at a pH of between 6.5 and 8.5 and binds to tissue; and wherein x is an integer of greater than or equal to 5, y is an integer of greater than or equal to 3, and z is an integer of greater than or equal to 0;

wherein the polymer has a molecular weight of at least 300 g/mole.

2. The method of claim 1 wherein the a biocompatible polymeric material is a block copolymer having the formula (A)x(B)y.

3. The method of claim 1 wherein the polymeric material further comprises a region C that is subject to degradation in vivo by hydrolysis, enzymatic degradation, or oxidation.

4. The method of claim 1 wherein the tissue binding region (B)y converts to a non-tissue binding region when exposed to water, oxidation or to enzymatic attack.

5. The method of claim 1 wherein the non-tissue binding region (A)x converts to a tissue binding region when exposed to water, oxidation or to enzymatic attack.

6. The method of claim 1 wherein the polymeric material further comprises an agent which is biologically active in a patient.

7. The method of claim 1 wherein the surface is a tissue surface, and wherein the polymer is applied to the tissue surface to inhibit tissue adhesion, thrombus formation, restenosis, or metastasis at the surface.

8. The method of claim 7 wherein the surface is a region of a tissue surface that has been surgically cut.

9. The method of claim 1 wherein the surface is the lining of a damaged blood vessel, and wherein the polymer is applied to the surface to inhibit thrombosis or adhesion at the lining of a blood vessel that has been damaged.

10. The method of claim 1 wherein the surface is a tissue surface, and wherein the polymer is applied to the tissue surface to inhibit attachment of cancerous or tumor cells.

11. The method of claim 7 wherein the surface is injured tissue of an organ or lumen of the body which contacts other organs that have also been injured.

12. The method of claim 1 wherein the polymer further comprises an agent which is biologically active in a patient, and wherein the polymer is targeted to attach to specific cell types by the agent.

13. The method of claim 1 wherein the surface is a tissue surface that has been chemically fixed or cryopreserved.

14. The method of claim 1 wherein (A)x and (A)z are selected from the group consisting of poly(oxyalkylene oxides), poly(ethyloxazoline), poly(N-vinyl pyrrolidone), poly(vinyl alcohol), neutral poly(amino acids) and copolymers of monomers selected from the group consisting of oxyalkylene oxides, ethyloxazoline, N-vinyl pyrrolidone, vinyl alcohol, and amino acids.

15. The method of claim 1 wherein (B)y is selected from the group consisting of poly(ethyleneimine), quaternary amines, and polyamines having amine groups on either the polymer backbone or the polymer sidechains.

16. The method of claim 1 wherein the tissue binding region (B)y is formed by polymerization of amides or esters.

17. The method of claim 1 where the non-tissue binding region (A)x is polyanionic and soluble in water.

18. The method of claim 6 wherein the polymeric material is biodegradable, and the biologically active agent is a component which is released as the polymer degrades.

19. The method of claim 6 wherein the biologically active agent is chemically coupled to the polymer.

20. The method of claim 7 wherein the biocompatible polymeric material is applied to the tissue surface in combination with a pharmaceutically acceptable carrier.

21. The method of claim 1 wherein the surface is a tissue surface and wherein the application of the polymer to the surface inhibits the attachment of cancer cells or platelets to the tissue surface.

22. The method of claim 1 wherein the surface is the surface of a tissue at a site of injury to the tissue, and wherein the application of the polymer to the surface enhances the binding of epithelial cells to the injured site.

23. The method of claim 1 wherein the surface is selected from the group consisting of an injured blood vessel, a surgical anastomosis, an injured serosal surface, a corneal injury and a skin wound.

24. The method of claim 1 wherein the surface is selected from the group consisting of an injured tissue site and an implant surface.

25. The method of claim 1 wherein the surface is the surface of a second cell, and wherein the method comprises applying the polymer to the second cell thereby to inhibit or enhance contact of the cells.

* * * * *